(12) United States Patent
Cohen et al.

(10) Patent No.: US 6,839,594 B2
(45) Date of Patent: Jan. 4, 2005

(54) ACTUATION AND CONTROL OF LIMBS THROUGH MOTOR NERVE STIMULATION

(75) Inventors: Ehud Cohen, Ganei Takva (IL); Yossi Gross, Moshav Mazor (IL)

(73) Assignee: Biocontrol Medical LTD, Yehud (IL)

( * ) Notice: Subject to any disclaimer, the term of this patent is extended or adjusted under 35 U.S.C. 154(b) by 221 days.

(21) Appl. No.: 09/843,334

(22) Filed: Apr. 26, 2001

(65) Prior Publication Data

US 2002/0161415 A1 Oct. 31, 2002

(51) Int. Cl.[7] ................................................ A61N 1/18
(52) U.S. Cl. ...................................................... 607/48
(58) Field of Search ......................... 607/2, 45, 72–76, 607/46, 48

(56) References Cited

U.S. PATENT DOCUMENTS

| | | | |
|---|---|---|---|
| 4,019,518 A | 4/1977 | Maurer et al. ............... 128/419 |
| 4,392,496 A | 7/1983 | Stanton ....................... 128/423 |
| 4,535,785 A | 8/1985 | van den Honert et al. .. 128/746 |
| 4,602,624 A | 7/1986 | Naples et al. ............... 128/784 |
| 4,608,985 A | 9/1986 | Crish et al. ................. 128/419 |
| 4,019,518 A | 10/1986 | Maurer et al. ............... 128/419 |
| 4,628,942 A | 12/1986 | Sweeney et al. ............ 128/784 |
| 4,632,116 A | 12/1986 | Rosen et al. ................ 128/419 |
| 4,649,936 A | 3/1987 | Ungar et al. ................ 128/784 |
| 4,926,865 A | 5/1990 | Oman ......................... 128/421 |
| 5,069,680 A | 12/1991 | Grandjean .................... 623/3 |
| 5,178,161 A | 1/1993 | Kovacs ....................... 128/784 |
| 5,199,430 A | 4/1993 | Fang et al. .................. 128/419 |
| 5,215,086 A | 6/1993 | Terry, Jr. et al. ............ 128/421 |
| 5,263,480 A | 11/1993 | Wernicke et al. ........... 607/118 |
| 5,282,468 A | 2/1994 | Klepinski ................... 128/642 |
| 5,314,495 A | 5/1994 | Kovacs ......................... 623/25 |
| 5,505,201 A | 4/1996 | Grill, Jr. et al. ............. 128/642 |
| 5,748,845 A | 5/1998 | Labun et al. ................. 395/20 |
| 5,776,171 A | 7/1998 | Peckham et al. ............. 607/48 |
| 5,954,758 A | 9/1999 | Peckham et al. ............. 607/48 |
| 6,026,328 A | 2/2000 | Peckham et al. ............. 607/48 |
| 6,066,163 A * | 5/2000 | John ............................. 607/45 |
| 6,086,525 A | 7/2000 | Davey et al. ................. 600/13 |
| 6,091,977 A | 7/2000 | Tarjan et al. ................ 600/372 |
| 6,104,960 A | 8/2000 | Duysens et al. ............. 607/117 |
| 6,119,516 A | 9/2000 | Hock ........................ 73/379.01 |
| 6,146,335 A | 11/2000 | Gozani ....................... 600/554 |
| 6,366,813 B1 * | 4/2002 | DiLorenzo ................... 607/45 |
| 6,405,079 B1 * | 6/2002 | Ansarinia ..................... 607/2 |
| 6,463,328 B1 * | 10/2002 | John ............................. 607/45 |

OTHER PUBLICATIONS

Evetovich T.K. et al., "Gender comparasions of the mechanomyographic responses to mimal concentric and eccentric isokinetic muscle actions", *Medicine & Science in Sports & Exercise*, 1998, 30(12), pp 1697–1702.

Pat AP; "*Method and Apparatus for Selective Control of Nerve Fibers*", Filed Apr. 4, 2001.

Cohen and Ayal, "*Selective control of nerve fibers*", Filed Jan. 2, 2001, Prov. Pat #60/263,834.

* cited by examiner

*Primary Examiner*—Jeffrey R. Jastrzab
(74) *Attorney, Agent, or Firm*—Woodcock Washburn LLP (57) ABSTRACT

Apparatus for actuating a skeletal muscle of a patient is provided. The apparatus typically includes a plurality of electrodes, which are adapted to be placed in a vicinity of a motor nerve that innervates the skeletal muscle. A control unit, is preferably adapted to drive a current between two or more of the plurality of electrodes, and to configure the current such that a first subset of axons in the nerve is excited by the current and such that a second subset of axons in the nerve is not excited by the current.

12 Claims, 4 Drawing Sheets

ACTUATION AND CONTROL OF LIMBS THROUGH MOTOR NERVE STIMULATION

FIELD OF THE INVENTION

The present invention relates generally to methods and devices for control of a limb on the body of a subject, and specifically to medical methods and devices for actuation and control of a limb by stimulation of motor nerves.

BACKGROUND OF THE INVENTION

Two hundred thousand Americans are alive today who suffer from the chronic effects of spinal cord injury. Traumatic brain injury is the source of 500,000 hospitalizations every year in the United States, and each year 80,000 of these patients will retain a lifelong disability.

There are two general types of spinal cord injury: complete and incomplete lesions. Complete lesions leave the patient with no motor, sensory, or autonomic function below the level of the lesion. Transection of the spinal cord is the most obvious cause of a complete lesion. The level of the injury in the spinal cord determines exactly what function will be lost, as the spinal nerves which exit the cord below this are absolutely unable to transmit signals to or from the brain. Incomplete lesions can take a variety of forms, and depending on the nature of the trauma, a range of motor and sensory abilities may be present.

Additionally, non-traumatic pathologies such as stroke and Parkinson's disease are also often characterized by a patient's inability to successfully translate a desire to perform an action into the appropriate motions of the relevant limbs. In summary, central nervous system pathologies are often responsible for varying levels of paralysis which cause immense suffering in the affected population.

Rehabilitation efforts for these patients usually focus on teaching means for using still-functioning limbs to carry out desired tasks, while trying, when possible, to recover some function in the affected limbs. In addition, a range of technologically advanced, expensive, and—unfortunately—not very satisfactory devices have been built and tested on patients. Amongst these are muscle-stimulation devices, which include electrodes that are mounted on a patient's muscles in a paralyzed limb. In response to a command, the electrodes drive current into the muscles, causing the contraction thereof. The resultant motion of the limb is typically rough, and the unnatural stimulation protocols often leave the patient's muscles tired, even after performing only a small number of tasks.

U.S. Pat. Nos. 5,178,161 and 5,314,495 to Kovacs, and U.S. Pat. No. 4,632,116 to Rosen, which are incorporated herein by reference, describe the use of microelectrodes to interface between control electronics and human nerves.

U.S. Pat. No. 4,649,936 to Ungar et al., which is incorporated herein by reference, describes an electrode cuff for placement around a nerve trunk, for generation of unidirectional propagating action potentials.

U.S. Pat. No. 4,019,518 to Maurer et al., which is incorporated herein by reference, describes methods for using an electrical stimulation system to selectively stimulate portions of the body.

U.S. Pat. Nos. 5,776,171 to Peckham et al., 5,954,758 to Peckham et al., and 6,026,328 to Peckham et al., which are incorporated herein by reference, describe methods and devices for stimulating muscles of limbs of the body, so as to achieve motion and control of the limbs in patients with central nervous system disabilities. Limb motions in each limb are commanded by external means and communicated via radio waves to apparatus implanted in the limb. Actual motion of the limb is monitored and compared to the commanded motion with the goal of attaining real-time control of the limb.

U.S. Pat. No. 5,748,845 to Labun et al., which is incorporated herein by reference, describes a device for controlling limbs of patients with central nervous system disabilities. The activity of a healthy muscle is sensed, analyzed, and used to determine input parameters to a control system of the device. Both external mechanical apparatus and direct electrical stimulation of muscle tissue are described as means for inducing movement of the disabled limb.

Many patents disclose other methods and devices for sensing muscular contractions and for applying muscular stimulation, including: U.S. Pat. Nos. 6,091,977 to Tarjan et al., 6,104,960 to Duysens et al., 6,086,525 to Davey et al., 4,926,865 to Oman, 4,392,496 to Stanton, and 6,146,335 to Gozani, which are incorporated herein by reference.

U.S. Pat. No. 6,119,516 to Hock, which is incorporated herein by reference, describes a biofeedback system, optionally including a piezoelectric element, which measures the motions of joints in the body.

U.S. Pat. No. 5,069,680 to Grandjean, which is incorporated herein by reference, describes the use of a piezoelectric crystal as a muscle activity sensor.

U.S. Pat. Nos. 4,602,624 to Naples et al., and 5,505,201 to Grill, Jr., et al., which are incorporated herein by reference, disclose techniques for making implantable electrodes.

In an article entitled, "Gender comparisons of the mechanomyographic responses to maximal concentric and eccentric isokinetic muscle actions," *Medicine & Science in Sports & Exercise*, 30(12), December, 1998, pp. 1697–1702, which is incorporated herein by reference, experiments are described in which a piezoelectric crystal contact sensor was placed over the vastus lateralis muscle to sense the mechanical activity thereof.

SUMMARY OF THE INVENTION

It is an object of some aspects of the present invention to provide improved apparatus and methods for the actuation of a limb on the body of a subject.

It is a further object of some aspects of the present invention to provide apparatus and methods for the stimulation of motor nerves in the body of a subject.

It is yet a further object of some aspects of the present invention to provide apparatus and methods for the selective stimulation of sub-groups of axons in a motor nerve.

It is still a further object of some aspects of the present invention to provide improved apparatus and methods for the control of the motion of a limb on the body of a subject.

It is an additional object of some aspects of the present invention to provide improved apparatus and methods for using neural networks to control a limb on the body of a subject.

It is yet an additional object of some aspects of the present invention to provide improved apparatus and methods to train neural networks for use in the control of a limb on the body of a subject.

It is another object of some aspects of the present invention to provide improved apparatus and methods for inputting commands to a system for controlling a limb on the body of a subject.

It is an additional object of some aspects of the present invention to provide improved apparatus and methods for monitoring the disposition of a limb on the body of a subject using piezoelectric materials.

In preferred embodiments of the present invention, a device for actuating a limb on the body of a subject comprises: (a) a motor nerve activation array, placed adjacent to at least one motor nerve which innervates a muscle controlling the limb, and (b) a control unit, coupled to the motor nerve activation array, which causes a current to pass through the activation array into the motor nerve. Typically, the control unit drives the current in order to stimulate one, some, or all of the axons in the motor nerve, thereby causing contraction of the muscle which controls the limb. Preferably, the control unit comprises circuitry which regulates the magnitude, frequency, and/or duration of the electric field generated by individual electrodes within the activation array.

It will be appreciated that whereas preferred embodiments of the present invention are described herein with respect to controlling a limb, the word "limb" is to be understood in the context of the present patent application and in the claims as including any part or parts of the body which are under voluntary control. Similarly, although in the specification and the claims desired motions of a limb are generally portrayed as resulting from stimulation of a single motor nerve, it will be appreciated that for many applications, a plurality of arrays may be coupled to one or more motor nerves, and driven so as to produce smooth and/or complex motions of one or more limbs.

In a preferred application of the present invention, the device is used by a subject who has an injury or other defect of the central nervous system, characterized by an inability to translate a conscious intention to cause a desired motion into actual nervous signals conveyed by motor nerves supplying the appropriate muscles. The stimulation applied by the activation array to individual axons or to groups of axons in the motor nerve is preferably configured, spatially and temporally, so as to induce electrical activity in the motor nerve that generates a desired contraction of relevant muscles. Actuation of a limb in this manner typically provides a generally natural movement of the limb, including fine motion and control. Prior art electrical techniques for actuating healthy limbs in subjects with central nervous system damage primarily involve the direct stimulation of muscular tissue, which does not allow for the fine motion or control of the limb typically provided by these embodiments of the present invention.

Alternatively or additionally, the device is used by a subject who has a tremor, such as an essential tremor. In these applications, one or more sensors (e.g., accelerometers or sensing electrodes) are preferably coupled to the subject so as to generate signals indicative of the onset of tremor. Preferably, the activation array applies signals to the motor nerve which are configured to reduce or eliminate the detected tremor. A feedback system is typically operative in the device to continuously analyze the outputs of the sensors, so as to determine to what extent the tremor has been reduced in response to the electrical stimulation by the activation array. Parameters of the applied signals are preferably modified in real time, responsive to the sensor signals, until the indications of tremor are reduced or substantially eliminated. Further preferably, the signals applied by the activation array to the motor nerve are configured so as to simulate physiological forms of efferent stimulation of the one or more muscles experiencing the tremor, thereby minimizing or eliminating the tremor.

For some applications, electrodes or electrode arrays are applied essentially directly to muscles which commonly experience tremor, and are driven to apply electric currents configured to control tremor. These techniques of direct muscle stimulation may be applied, as appropriate, in conjunction with or separately from the tremor-control techniques using nerve stimulation that are described herein. It is to be understood that although many preferred embodiments of the present invention are described herein with respect to enabling or enhancing motion of generally paralyzed limbs, these techniques may also be applied, mutatis mutandis, to treating tremor.

In preferred embodiments of the present invention, individual axons or small groups of axons in a motor nerve are selectively stimulated by the application of a voltage between two or more electrodes in the activation array. The electrodes and the applied voltage are preferably configured so as to create an electric field that has a distribution of electric potential that only exceeds the firing threshold of axons at desired locations in the nerve. With appropriate temporal and spatial modulation of the electric field applied by some or all of the electrodes in the activation array, controlled actuation of a limb is accomplished, preferably in a manner analogous to that which characterizes muscular actuation in a subject with a healthy central nervous system.

In some preferred embodiments of the present invention, the activation array comprises a ring of electrodes, adapted to be fitted around a selected motor nerve. The electrodes are coupled to the control unit, which applies appropriate temporally-varying voltages to individual electrodes in the electrode array, so as to create electric fields that stimulate selected axons in the nerve bundle in a manner appropriate for actuating the desired limb.

In further preferred embodiments of the present invention, the activation array is formed by techniques analogous to those used in the fabrication of computer chips. For example, techniques known to those skilled in the art may be utilized in the fabrication of electrode arrays with inter-electrode distances on the scale of hundreds of microns or millimeters. Preferably, logic circuitry including a programmable microprocessor is adapted to control the voltages applied to the individual electrodes, so as to generate the electric field described hereinabove. As appropriate, methods and apparatus described in one or more of the patents cited in the Background section of the present patent application may be applied, mutatis mutandis, in carrying out some of the embodiments of the present invention.

In still further preferred embodiments of the present invention, an array of electromagnets is arranged in the vicinity of a designated motor nerve. The array is coupled to the control unit, which drives the array to create a varying magnetic field that induces electric currents in the nerve bundle. These currents, in turn, stimulate desired axons in the nerve bundle in an appropriate spatio-temporal manner in order to achieve a designated motion of the limb.

In some further preferred embodiments of the present invention, the control unit comprises logic circuitry and software that receives an input command from the subject, and induces, responsive thereto, a desired movement of the limb. For example, a "Hand forward" command may cause the control unit to activate the motor nerve activation array in such a manner that the subject's hand moves forward.

Preferably, a calibration procedure of the device includes stimulating an individual axon or a group of axons in a designated motor nerve, and observing the subsequent motion of the limb whose muscles are innervated by the motor nerve. Calibration software preferably modifies the stimulation parameters (e.g., amplitude, duration, frequency), and determines a set of operating parameters appropriate for carrying out desired motions of the limb. The parameters are preferably intermittently upgraded during subsequent calibration procedures.

For some applications, the control unit comprises an artificial neural network, which learns how to control the limb through selective stimulation of individual axons or groups of axons in motor nerve bundles. Stimulating one or more axons and monitoring the response of the limb preferably provides training inputs to a network modification algorithm, which, in turn, allows for the continual modification of the various weights in the neural network, leading to improved movement and control of the limb.

Some preferred embodiments of the present invention comprise a motion monitoring system to aid in the training of the neural network or other control algorithm. One preferred embodiment comprises accelerometers and/or other mechanical disposition sensors coupled to the limb and to the control unit, such that the disposition of the limb can be monitored during actuation of the limb. Preferably, the limb's acceleration and velocity are controlled so as to generally minimize the time for a given maneuver, while keeping the acceleration of the limb within acceptable limits and/or while minimizing energy expended during the maneuver. Training of the neural network is preferably achieved by repeating the same maneuver, while varying the strength of the neural connections using techniques known in the art, until, for example, the time for execution of a particular maneuver is reduced to an acceptable level.

In another preferred embodiment, the device comprises a goniometer for measuring the angles of joints of the limb, allowing the orientation of the limb to be determined during movement thereof. It is noted that motion planning for certain maneuvers of the limb is relatively simple, when the motion can be specified in terms of joint angles. For many applications, a plurality of goniometers are included in the device, and may be conveniently integrated into, for example, a glove such as the CyberGlove (Virtual Reality Technologies GmbH, Germany), so as to enable a determination of the joint angles at a plurality of joints in the hand and wrist.

In still another preferred embodiment, the mechanical disposition sensor comprises a piezoelectric sensor, adapted to be coupled to muscle tissue or other tissue of the subject. Typically, the piezoelectric sensor generates a current responsive to a level of contraction of the muscle tissue, and the control unit analyzes the current to determine the mechanical forces developed in the muscle tissue in response to stimulation of axons in the motor nerve by the motor nerve activation array. Preferably, a control system of the device assesses in advance the forces needed for execution of a particular task, and compares these in real time to those actually being generated and indirectly sensed by the piezoelectric sensor. This approach is particularly beneficial for tasks in which resistance must be overcome by the limb during a task. For example, if a finger is "commanded" to push a button that has a known resistance, it is efficient to specify the force to be applied by the finger, and to frequently compare the specified force with the forces generated during execution of the task.

For applications in which the subject has unilateral dysfunction (e.g., secondary to a stroke), a piezoelectric sensor or other suitable sensor is preferably also coupled to corresponding muscle tissue in the subject's functioning contralateral limb, such that the forces developed in the functioning muscle tissue during a designated maneuver can be determined. This information is used to drive the motor nerve activation array to apply current to the nerve so as to develop the same forces in the muscle tissue of the contralateral limb.

Preferably, the device comprises a command input unit which allows the subject, who typically has some degree of physical disability, to command that a desired action be executed by a disabled limb. Further preferably, the input unit responds to verbal commands of the subject, such as "Lift hand." Alternatively or additionally, a joy stick or other mechanical device is used to input commands to the disabled limb.

Further alternatively or additionally, the command input unit comprises a device which responds to light inputs. For example, shining a light beam on an object may be a cue for the limb to move towards that object. Small lasers are preferably used as the light source, such that detectors, tuned to a fixed frequency of light, eliminate spurious inputs due to other light sources. As appropriate, the lasers are maneuvered by a healthy limb, attached to a pair of eyeglasses, or even manipulated responsive to movement of the subject's tongue, depending on the degree of physical disability.

There is therefore provided, in accordance with a preferred embodiment of the present invention, apparatus for actuating a skeletal muscle of a patient, including:

a plurality of electrodes, which are adapted to be placed in a vicinity of a motor nerve that innervates the skeletal muscle; and a control unit, which is adapted to drive a current between two or more of the plurality of electrodes, and to configure the current such that a first subset of axons in the nerve is excited by the current and such that a second subset of axons in the nerve is not excited by the current.

Preferably, but not necessarily, the plurality of electrodes includes at least 15 electrodes. Alternatively or additionally, at least two of the plurality of electrodes are spaced less than 2 mm apart.

In a preferred embodiment, the plurality of electrodes are adapted to be implanted in the patient and to be placed in contact with the motor nerve. For example, the plurality of electrodes may be disposed around the motor nerve.

Preferably, the control unit is adapted to configure the current such that the skeletal muscle is induced to contract responsive to the current, and such that another skeletal muscle of the patient, which other skeletal muscle is innervated by the second subset of axons, substantially does not contract responsive to the current.

Further preferably, the plurality of electrodes includes a first set of electrodes, wherein the motor nerve includes a first motor nerve, wherein the skeletal muscle includes a first skeletal muscle, wherein the apparatus includes a second set of electrodes, which are adapted to be placed in a vicinity of a second motor nerve, which second motor nerve innervates a second skeletal muscle, and wherein the control unit is adapted to drive respective first and second currents through the first and second sets of electrodes, so as to induce a coordinated movement of a limb controlled by the first and second muscles.

In a preferred embodiment, the control unit is adapted to drive respective first and second currents through the plurality of electrodes, responsive to respective first and second sets of stimulation parameters adapted to induce modulation of respective first and second sets of axons in the motor nerve, so as to induce a coordinated movement of a limb having one or more muscles innervated by the motor nerve.

Alternatively or additionally, the control unit is adapted to drive the current using a first set of stimulation parameters in order to induce contraction of a first set of muscle fibers in a muscle innervated by the nerve, and, subsequent thereto, to drive the current using a second set of stimulation parameters, in order to induce contraction of a second set of muscle fibers in the muscle. Typically, the control unit cycles between applying the current using the first set of stimulation parameters and applying the current using the second set of stimulation parameters, in accordance with a schedule determined to reduce fatigue of the muscle.

Typically, the apparatus includes a user-interface unit, which is adapted to convey an instruction from the patient to the control unit. In a preferred embodiment, the user-interface unit is adapted to communicate with the control unit by means of wireless communication. If appropriate, the user-interface unit may be adapted to receive the instruction by means of a voice command from the patient.

In a preferred embodiment, the user-interface unit includes an eye-blink sensor, which is adapted to detect eye-blinking by the patient, and the user-interface unit is adapted to convey the instruction responsive to an output of the eye-blink sensor. Alternatively or additionally, the user-interface unit includes a pupil tracking unit, which is adapted to detect movement of a pupil of an eye of the patient, and the user-interface unit is adapted to convey the instruction responsive to an output of the pupil tracking unit.

In a preferred embodiment, the user-interface unit includes:
- a focused-energy source, adapted to be directed by the patient at a target; and
- an energy detector, adapted to detect energy generated by the source and reflected by the target, and adapted to generate a detector signal responsive to the detected energy,
- wherein the control unit is adapted to receive the detector signal, to analyze the detector signal, and to drive the current responsive to analyzing the detector signal.

The focused-energy source may include, for example, a laser and/or an ultrasound source.

Preferably, the apparatus includes a disposition sensor, which is adapted to generate a disposition sensor signal responsive to a disposition of a limb of the patient which includes the skeletal muscle, and the control unit is adapted to analyze the disposition sensor signal and to drive the current responsive to analyzing the signal.

In some preferred embodiments of the present invention, the sensor includes one or more of the following:
- an accelerometer, e.g., a linear accelerometer or a three-axis accelerometer,
- a sensing electrode, adapted to sense a contraction of the skeletal muscle,
- a video imaging unit,
- an ultrasound transducer,
- an ultrasound triangulation transducer,
- a force transducer,
- a piezoelectric element, or
- a goniometer.

In a preferred embodiment, the disposition sensor includes a first disposition sensor which is adapted to generate a first disposition sensor signal,
wherein the limb includes a first limb,
wherein the apparatus includes a second disposition sensor, adapted to generate a second disposition sensor signal responsive to a disposition of a second limb of the patient, the second limb being contralateral to the first limb, and
wherein the control unit is adapted to analyze the first and second disposition sensor signals and to drive the current responsive to analyzing the signals.

For some applications, the apparatus includes a glove designated to be worn on a hand of the patient,
wherein the glove includes a plurality of disposition sensors which are adapted to generate respective disposition sensor signals responsive to dispositions of respective portions of the hand, and
wherein the control unit is adapted to drive the current responsive to the plurality of disposition sensor signals.

Preferably, the control unit is adapted to analyze the disposition sensor signal using an artificial neural network algorithm.

The control unit is typically adapted to modify a frequency, amplitude, and/or duration of the current responsive to analyzing the disposition sensor signal.

There is further provided, in accordance with a preferred embodiment of the present invention, apparatus for actuating a skeletal muscle of a patient, including:
- a plurality of electromagnetic elements, which are adapted to be placed in a vicinity of a motor nerve that innervates the skeletal muscle; and
- a control unit, which is adapted to drive the electromagnetic elements to generate a varying magnetic field that induces an electric current in the motor nerve, and to configure the field such that a first subset of axons in the nerve is excited by the current and such that a second subset of axons in the nerve is not excited by the current.

Preferably, the control unit is adapted to configure the field such that the skeletal muscle is induced to contract responsive to the induced current, and such that another skeletal muscle of the patient, which other skeletal muscle is innervated by the second subset of axons, substantially does not contract responsive to the induced current.

Further preferably, the apparatus includes a disposition sensor, which is adapted to generate a disposition sensor signal responsive to a disposition of a limb of the patient which includes the skeletal muscle, wherein the control unit is adapted to analyze the disposition sensor signal and to modify the field responsive to analyzing the signal.

There is still further provided, in accordance with a preferred embodiment of the present invention, apparatus for controlling a limb of a patient, including:
- one or more electrodes, which are adapted to be placed in a vicinity of a motor nerve that innervates a skeletal muscle that controls the limb;
- a disposition sensor, which is adapted to generate a disposition sensor signal responsive to an actual disposition of the limb; and
- a control unit, which is adapted to receive the disposition sensor signal, to determine, responsive thereto, the actual disposition of the limb, and to drive the one or more electrodes to apply a current to the nerve, configured such that application thereof induces a contraction of the skeletal muscle which reduces a difference between a desired disposition of the limb and the actual disposition of the limb.

In a preferred embodiment, the disposition sensor is adapted to generate the disposition sensor signal responsive to a tremor of the limb.

For some applications, the control unit is adapted to drive first and second ones of the one or more electrodes to apply respective first and second electrical signals to the nerve responsive to analyzing the disposition sensor signal.

In a preferred embodiment, the one or more electrodes include a first set of electrodes,
wherein the motor nerve includes a first motor nerve,
wherein the skeletal muscle includes a first skeletal muscle,
wherein the apparatus includes a second set of electrodes, which are adapted to be placed in a vicinity of a second motor nerve, which second motor nerve innervates a second skeletal muscle, and
wherein the control unit is adapted to drive respective first and second currents through the first and second sets of electrodes, responsive to the disposition sensor signal, so as to induce a coordinated movement of the limb.

There is still further provided, in accordance with a preferred embodiment of the present invention, apparatus for treating tremor of a muscle, including:
a plurality of electrodes, which are adapted to be placed in a vicinity of a nerve that innervates the muscle;
a sensor, which is adapted to generate a signal responsive to tremor of the muscle; and
a control unit, which is adapted to receive the signal and, responsive thereto, drive the electrodes to apply a current to the nerve, configured so as to stimulate afferent axons of the nerve.

In a preferred embodiment, the sensor includes one of the plurality of electrodes. Alternatively or additionally, the sensor includes at least one electromyographic (EMG) electrode. For some applications, the at least one EMG electrode includes two EMG electrodes, respectively adapted to be coupled to sense electrical activity of the muscle and a muscle antagonistic thereto.

Preferably, the plurality of electrodes are adapted to be disposed at respective sites along the length of the nerve. Typically, the control unit drives the electrodes in a sequence, responsive to the proximity of each electrode on the nerve to the brain.

There is yet further provided, in accordance with a preferred embodiment of the present invention, a method for actuating a skeletal muscle of a patient, including:
driving a current into a motor nerve that innervates the skeletal muscle; and
configuring the current such that a first subset of axons in the nerve is excited by the current and such that a second subset of axons in the nerve is not excited by the current.

There is additionally provided, in accordance with a preferred embodiment of the present invention, a method for actuating a skeletal muscle of a patient, including:
generating a varying magnetic field that induces an electric current in a motor nerve that innervates the skeletal muscle; and
configuring the field such that a first subset of axons in the nerve is excited by the current and such that a second subset of axons in the nerve is not excited by the current.

There is yet additionally provided, in accordance with a preferred embodiment of the present invention, a method for controlling a limb of a patient, including:
sensing an actual disposition of the limb; and
driving a current into a motor nerve that innervates a skeletal muscle that controls the limb; and
configuring the current to induce a contraction of the skeletal muscle which reduces a difference between a desired disposition of the limb and the actual disposition of the limb.

There is still additionally provided, in accordance with a preferred embodiment of the present invention, a method for treating tremor of a muscle, including:
sensing tremor of the muscle; and
responsive thereto, applying a current to a nerve that innervates the muscle, configured so as to stimulate afferent axons of the nerve.

The present invention will be more fully understood from the following detailed description of the preferred embodiments thereof, taken together with the drawings, in which:

DETAILED DESCRIPTION OF PREFERRED EMBODIMENTS

Figure 1:
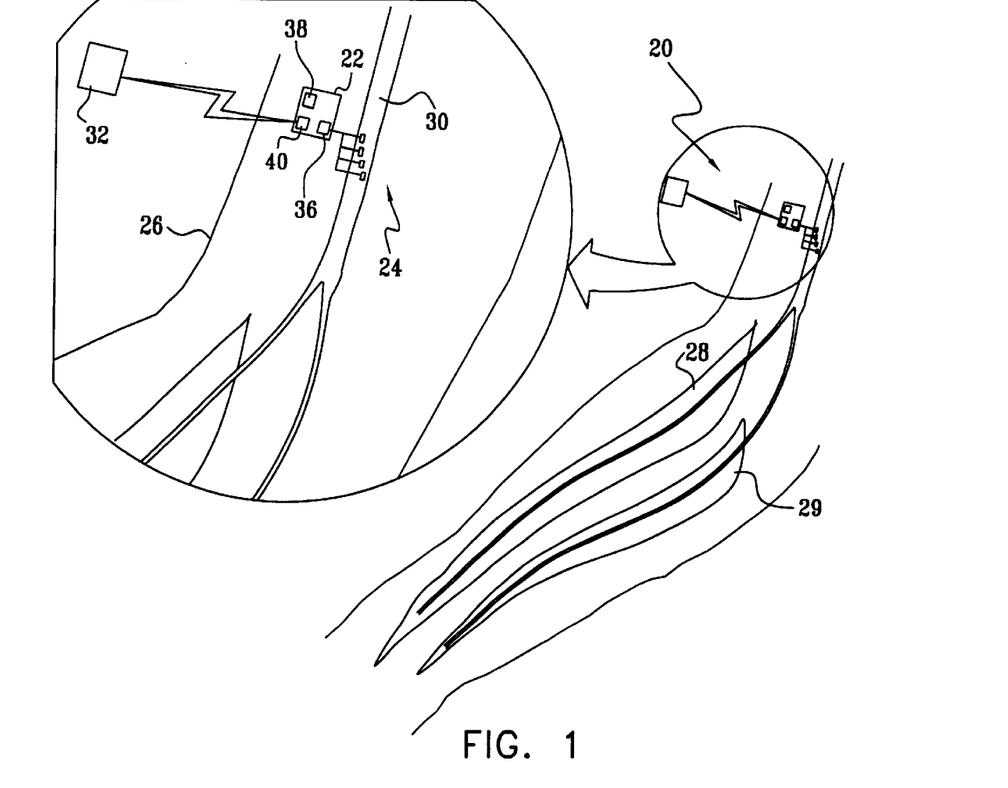
FIG. 1 is a schematic illustration of a device for actuation of a limb, in accordance with a preferred embodiment of the present invention.

FIG. 1 is a schematic illustration of a limb actuation device 20, in accordance with a preferred embodiment of the present invention. Device 20 preferably comprises an implanted control unit 22 which is coupled to an electrode array 24 comprising a plurality of microelectrodes. Array 24 is placed in a vicinity of a motor nerve 30 that innervates a skeletal muscle 28 of a limb 26. Device 20 preferably actuates limb 26 by stimulation of selective subsets of axons in motor nerve 30. For example, array 24 may be driven to excite axons in nerve 30 that stimulate muscle 28 to contract, while generally avoiding exciting axons in nerve 30 that would cause another muscle 29 to contract. Because axons are often aligned in tracts within a nerve, for some applications, the selective stimulation of axons is achieved by driving current through a selected tract by electrodes in array 24 which are near that tract. It is noted that motor nerves are typically characterized by some degree of redundancy in their axonal connections, such that desired limb motions can generally be attained even in the absence of individual control of every axon innervating the muscle.

Control unit 22 preferably comprises a signal generation unit 36, a battery or remote power source 38, and user-interface electronics 40. Preferably, but not necessarily, the battery is rechargeable using wired or wireless techniques known in the art. The user-interface electronics are preferably in wireless communication with an external user-interface unit 32, which typically comprises standard data input means such as buttons or a touch screen display, or other apparatus as described hereinbelow. In a simple embodiment, interface unit 32 initializes actuation of the limb and allows the subject to choose a particular motion or action. For some applications, a voice activation system of interface unit 32 permits the subject to enter voice commands, which are interpreted using techniques known in the art, to enable the subject's selection and initiation of a desired motion of the limb. Alternatively or additionally, interface unit 32 comprises an eye-blink sensor, adapted to generate a signal responsive to a number of blinks and/or a duration of one or more blinks. Further alternatively or additionally, unit 32 comprises a pupil tracking unit, which uses techniques known in the art to receive commands from the subject. It is to be understood that these particular examples of preferred interface units are described by way of illustration and not limitation, and that the scope of the present invention includes the use of other input means, not explicitly described herein, which would occur to a person of ordinary skill in the art upon reading the disclosure of the present patent application.

Preferably, signal generation unit 36 controls the magnitude and duration of the electric field generated by each microelectrode in electrode array 24, such that controlled, coordinated contractions are produced. When device 20 drives current through the selected subsets of axons of motor nerve 30, activation of the axons occurs, producing contraction of muscle tissue innervated by the stimulated axons. By inducing contraction of selected muscle fibers or sets of fibers, fine motor movement is achieved in a manner analogous to a healthy neuromuscular system. For many applications, muscle fibers within a single muscle are cyclically stimulated to contract in sequence, so as to reduce the development of fatigue in any one set of fibers. Similarly, individual muscles performing generally parallel functions can be cycled to hold a limb in a particular position, or move the limb to a new position, without engendering excess fatigue. Prior art devices for activation of muscle tissue, by contrast, generally involve stimulation of gross regions of muscle tissue, resulting in crude movement of limbs and rapid fatigue of the overworked muscle tissue.

Figure 2:
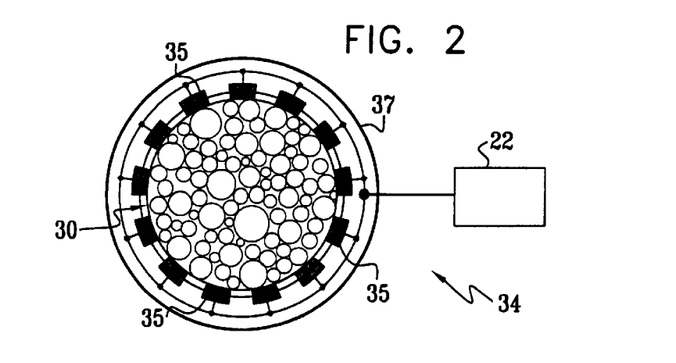
FIG. 2 is a schematic, sectional illustration of an electrode array, in accordance with a preferred embodiment of the present invention.

FIG. 2 is a schematic illustration (not to scale) of an array 34 for use with device 20, in accordance with a preferred embodiment of the present invention. Array 34 preferably comprises a ring of elements 35, typically g comprising microelectrodes or electromagnets, arranged so as to partially or completely surround motor nerve 30. Preferably, the array is coupled to a rigid frame 37, such that the locations of the elements relative to each other is generally fixed. Alternatively, individual electrodes or electromagnets are implanted so as to encircle the nerve. A plurality of arrays 34 are typically disposed along the length of nerve 30, and may be spaced on the nerve, by way of illustration and not limitation, with inter-array gaps of approximately 6 mm.

In applications in which elements 35 comprise electrodes, activation of a designated subset of axons in nerve 30 is preferably achieved by applying appropriate electric potentials to the elements, so as to raise the transmembrane potential of the designated axons above their threshold potentials, while generally avoiding such an elevation in axons of the nerve which are not in the subset of axons. For some applications, a desired electric field is specified, and control unit 22 determines appropriate electric potentials to be applied to each electrode in the array so as to generate the field. Preferably, the relative locations of the electrodes and the number of electrodes in the array are optimized based on the particular motor nerve to be stimulated.

In applications in which elements 35 comprise electromagnetic elements, control unit 22 preferably drives the array to create a varying magnetic field that induces electric currents at desired locations in the nerve bundle. These currents, in turn, stimulate appropriate groups of axons in nerve 30 in a controlled manner, in order to achieve a designated motion of the limb.

Figure 3:
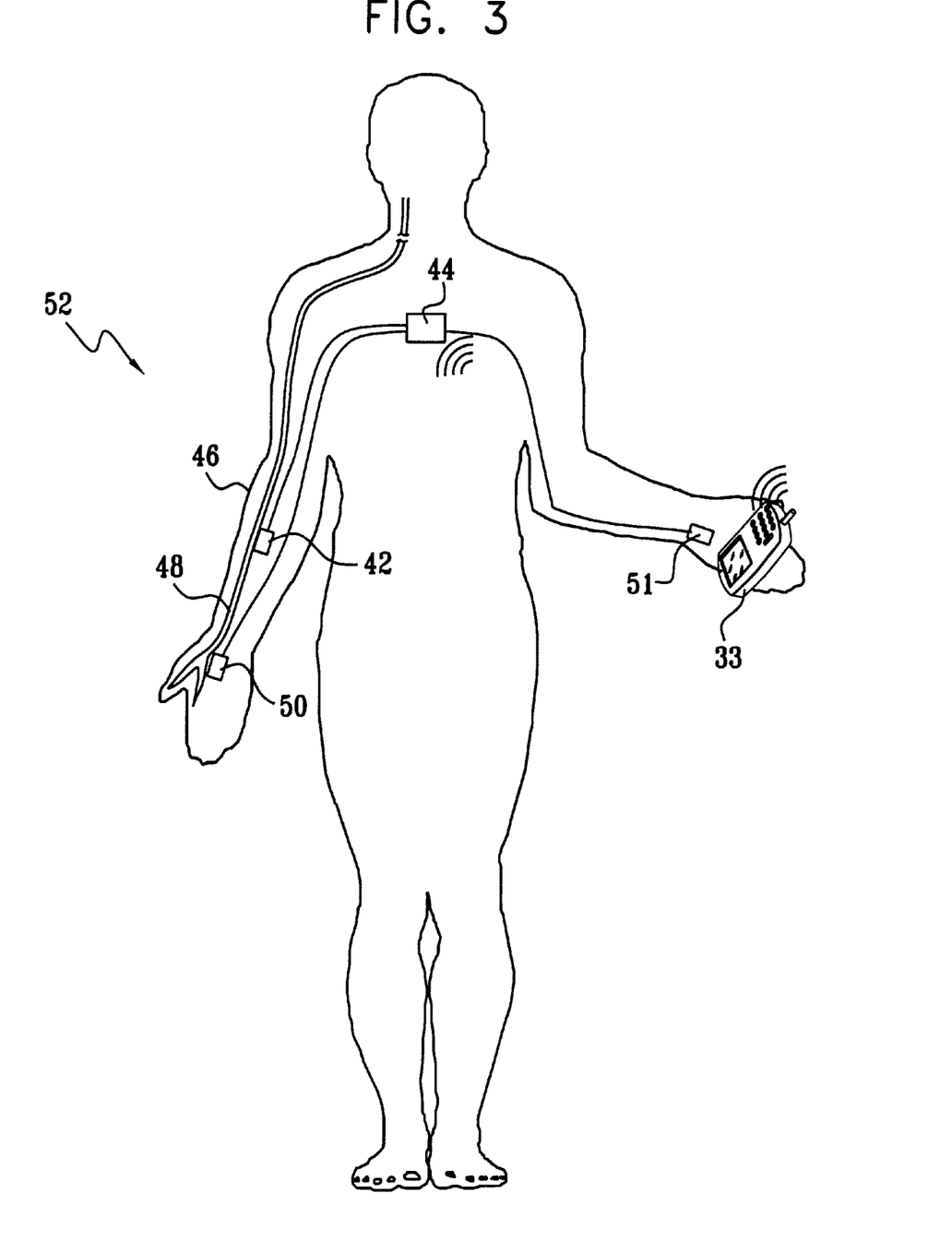
FIG. 3 is a schematic illustration of a device for the actuation and control of a limb, in accordance with a preferred embodiment of the present invention.

FIG. 3 is a schematic illustration of a device 52 for the actuation and control of a limb 46 on the body of a subject, in accordance with a preferred embodiment of the present invention. Device 52 comprises an electrode array 42, implanted in a vicinity of a motor nerve 48 of the subject, and at least one disposition sensor 50, typically implanted in or otherwise coupled to sense a disposition of the limb. A control unit 44 of device 52 is preferably adapted to determine the disposition of limb 46 based on a disposition sensor signal generated by sensor 50, and to drive electrode array 42 responsive to an analysis of the signal.

Preferably, disposition sensor 50 comprises an accelerometer, sensing electrode, force transducer, ultrasound transducer, video camera, or other sensor, such that, for example, the location, velocity and acceleration of the limb can be determined by control unit 44. Information indicative of the disposition of the limb is preferably used by the control unit to enable a determination of the difference between the actual disposition of the limb during a maneuver and a desired disposition. Control unit 44 preferably drives the electrodes in array 42 to stimulate axons in motor nerve 48 such that this difference is minimized during the maneuver. Thus, for example, in response to a command such as "Bring cup to mouth," the control unit preferably drives the electrodes to cause the limb to perform the specified motion, and actively controls the limb, via feedback from sensor 50, to ensure that the correct motion is achieved.

It is to be understood that, whereas preferred embodiments of the present invention are described for simplicity with respect to a single electrode array being applied to a single motor nerve, for many applications, a plurality of arrays may be used to stimulate a single nerve or a plurality of nerves, in order to achieve desired motions and/or to achieve a desired coordination of a particular motion. Alternatively or additionally, a particular electrode array applies to motor nerve 48 current having varying stimulation parameters, so as to selectively stimulate different axons within the nerve, and thereby attain desired motions or dispositions of limb 46. Moreover, although FIG. 3 shows a single disposition sensor 50 coupled to measure dispositions of the subject's dysfunctional limb, it is to be understood that it is within the scope of the present invention to utilize a plurality of such sensors.

It is to be further understood that although many preferred embodiments of the present invention are described herein with respect to enabling or enhancing motion of generally paralyzed limbs, these techniques may also be applied, mutatis mutandis, to treating tremor. For example, sensor 50 may comprise an accelerometer and/or an electrode, and may be coupled to limb 46 and enabled to generate signals indicative of the onset of tremor. Preferably, electrode array 42 applies signals to nerve 48 which are configured to reduce or eliminate the detected tremor. A feedback system of control unit 44 is typically operative to continuously analyze the outputs of sensor 50, so as to determine to what extent the tremor has been reduced in response to the electrical stimulation by the activation array. Parameters of signals applied by array 42 are preferably modified in real time, responsive to signals from sensor 50, until the indications of tremor are reduced or substantially eliminated.

For some applications, individual electrodes or one or more electrode arrays 42 are applied essentially directly to muscles (such as muscles 28 or 29) that are found to commonly experience tremor. Preferably, control unit 44 drives these electrodes or electrode arrays to apply electric currents that are configured to control a detected tremor. For example, mutually antagonistic muscles may be stimulated to contract in alternation to counter the tremor, in accordance with a schedule which initially minimizes and then essentially or completely neutralizes the tremor. These techniques of direct muscle stimulation may be applied, as appropriate, in conjunction with or separately from the tremor-control techniques using nerve stimulation that are described herein.

In a preferred embodiment for treating tremor, control unit 44 detects tremor based on signals from accelerometers and/or EMG electrodes in sensor 50. If appropriate, EMG electrodes may be coupled for this purpose to agonist and antagonist muscles for a specific joint. In response to detecting tremor, the control unit drives one or more electrode arrays 42 to stimulate afferent axons in nerve 48, such that action potentials are conducted towards the brain, which, in turn, cause the brain to reduce the efferent stimulation of muscle 48, thereby controlling the tremor. It is the inventors' belief that because tremor is a problem in the natural feedback loop connecting the muscle and the brain, it can be treated by modifying the behavior of the feedback loop. In particular, by generating and/or amplifying feedback from a limb to the brain, as described herein, the brain is given the correct impression that the limb is in the desired position, and further contractions are not necessary.

By contrast, in a subject whose tremor is not treated, the brain typically views the muscle as not being sufficiently contracted, and/or views the limb as not being near its destination. In these cases, the brain continues to cause muscular contractions, resulting in the limb significantly overshooting its target. In response to the overshoot, the brain drives an antagonistic muscle to contract, typically yielding a subsequent excessive movement. Repeated cycles of this behavior constitute the undesired tremor. In order to treat the tremor, this embodiment of the present invention interrupts these cycles by inducing and/or enhancing afferent action potentials, so that the subject experiences a slight feeling of vibration, and the brain interprets the enhanced afferent stimulation as indicating that the desired contractions or limb motions have already taken place. In response, the brain does not initiate the cycle of muscular contractions which are tremor.

Alternatively or additionally, control unit 44 reduces tremor by modifying the efferent stimulation of the muscle. For example, the control unit may inhibit contractions of one or more muscles, either through electric fields applied to the muscles themselves, or to one or more nerves innervating the muscles.

If appropriate, methods and apparatus disclosed in U.S. Provisional Patent Application No. 60/263,834 to Cohen and Ayal, entitled "Selective blocking of nerve fibers," which shares common inventorship with the inventorship of the present patent application and is incorporated herein by reference, may be adapted for use with tremor-control or limb-control techniques described herein. Alternatively or additionally, methods and apparatus disclosed in a US patent application filed Apr. 4, 2001, entitled "Method and apparatus for selective control of nerve fibers," to Cohen and Ayal, which shares common inventorship with the present patent application and is incorporated herein by reference, may be adapted for use with tremor-control or limb-control techniques described herein. Further alternatively or additionally, methods and apparatus described in the above-cited U.S. Pat. No. 4,649,936 to Ungar et al. are adapted for use with this or other preferred embodiments of the present invention. For example, in order to enhance afferent action potentials and thereby modify a malfunctioning feedback loop, techniques described in one or both of these applications may be used to selectively stimulate large diameter afferent axons. Typically, electrodes placed along the length of a nerve apply a wave of depolarizing or hyperpolarizing electrical energy to the nerve, which wave is configured to move along the nerve in a desired direction at a rate generally equivalent to the conduction velocity of fibers having a particular diameter. In this manner, for example, depolarizing energy moving along the length of the nerve at a high speed will tend to continually depolarize large diameter axons, inhibiting the propagation of action potentials therein, while smaller axons with lower natural conduction velocities will be substantially unaffected by the applied energy.

For limb control applications, a control algorithm relating the electrode potentials to the various dispositions of the limb is typically utilized. Preferably, as described hereinbelow, an artificial neural network is used in determining parameters for the control algorithm, such that the subject is enabled to actuate and control the limb through even relatively complex motions. For example, the subject could push one button on a handheld user-interface unit 33 to select forward movement of the limb, and another button to select the distance that the limb is to be moved. Alternatively or additionally, verbal or other inputs are used to command the same motion of the limb.

Preferably, training of the neural network is accomplished using techniques generally known in the art for determining the weights that govern the behavior of a neural network based on a range of possible inputs and desired outputs. For the purposes of these embodiments of the present invention, various subsets of axons in the motor nerve are stimulated, and the resulting dispositions of the limb are determined using sensor 50, and fed back to control unit 44. If appropriate, a parallel disposition sensor 51 is coupled to the subject's healthy contralateral limb, and the subject issues a command and then moves the healthy limb in a manner in which it is desired that the dysfunctional limb should learn to respond to the command. Thus, for example, during calibration of device 52, sensors 50 and 51 may be incorporated into gloves worn respectively on the subject's dysfunctional and functional hands, and in goniometers coupled to the subject's elbows and shoulders. When the subject issues the command "Raise hand to mouth," she consciously causes her healthy limb to carry out the designated motion, and the neural network subsequently modifies its own weighting structure such that current applied by electrode array 42 causes limb 46 to perform the desired maneuver (typically after at least several training iterations).

If appropriate, disposition sensors 50 and 51 may alternatively or additionally be integrated into an ultrasonic locating system, using triangulation or other methods and apparatus known in the art, such that consciously-generated movements of the healthy contralateral limb may be measured and compared to those induced in limb 46 responsive to the signals applied by array 42. Further alternatively or additionally, video motion analysis hardware and software known in the art are utilized in tracking the motions of the healthy and dysfunctional limb, in order to facilitate calibration of device 52. It will be appreciated that in some environments, e.g., in the subject's home and office, the video and/or ultrasonic tracking techniques can also be used during regular operation of the device, either in combination with or separately from the feedback provided by sensors which are typically implanted (such as accelerometers). Additionally, for some applications, ultrasonic transducers are mounted to various sites on the subject's body, and allow control unit 44 to determine relative positions and motions of these sites with respect to each other, and, subsequently, to determine whether appropriate limb motions are occurring in response to applied stimulation.

Preferably, by starting with simple training commands (e.g., "Close hand," "Pronate forearm," "Flex wrist," "Move to the right," or "Increase pressure on object"), which can be performed initially without fine control, a basic neural network command database is initially established. Subsequently, continued training of the neural network is typically based on combining the movements in the basic database so as to lead to improved limb control during more complex maneuvers (e.g., "Type S-A-V-E SPACEBAR F-I-L-E," or "Double click left mouse button"). Preferably, training of the neural network continues during regular operation, based on analyzing commands input to the device and the subsequent response of the limb, so as to lead to continual improvement in the function of the limb.

For some applications, the subject herself may assign a grade to the induced response of the dysfunctional limb to a given command. This grade (e.g., 1—poor, to 4—very good), which may be entered into a user-interface unit 33, is preferably used in conjunction with multivariate optimization techniques known in the art to determine optimal protocols for driving the individual electrodes in array 42 to stimulate appropriate axons of motor nerve 48. Typically, determining the protocols includes evaluating different sequences for stimulating the various electrodes, varying the waveforms to cover a range of waveform shapes known in the art, and ascertaining signal magnitudes and timing parameters which yield movements of the limb having consistently high grades.

In some training procedures for device 52, the subject issues a command (e.g., "Flex elbow"), and control unit 44 executes the command twice, using different stimulation protocols determined in accordance with a designated multivariate optimization technique. The subject grades the resultant movements by selecting from a menu consisting of the following entries comparing the first movement to the second movement: {"much worse", "worse", "no change", "better", and "much better"}. In subsequent iterations, control unit 44 varies different values governing the stimulation, until the subject indicates that the movement of the limb is satisfactory.

Figure 4:
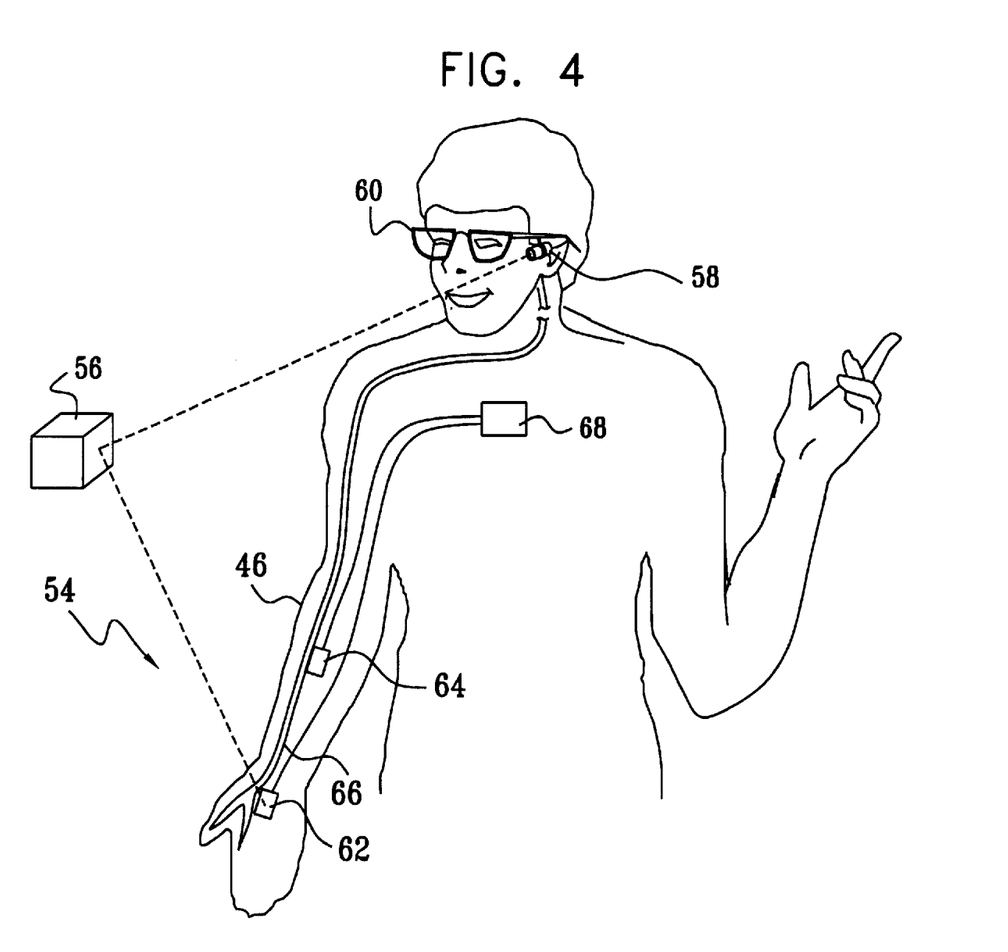
FIG. 4 is a schematic illustration of control apparatus of a device for the actuation and control of a limb, in accordance with a preferred embodiment of the present invention.

FIG. 4 is a schematic illustration of another device 54 for actuation and control of a limb on the body of a subject, in accordance with a preferred embodiment of the present invention. Device 54 comprises an electrode array 64, applied to or in a vicinity of a motor nerve 66 that innervates one or more skeletal muscles controlling motion of the limb. Array 64 is preferably coupled to a control unit 68, which controls the electric potential at each electrode in electrode array 64. Device 54 typically stimulates the subject's skeletal muscle via controlled stimulation of motor nerve 66, in a manner similar to that described hereinabove with respect to device 20 and/or device 52.

Device 54 differs from devices 20 and 52, however, in the manner in which a desired motion of the limb is communicated to the device. Preferably, device 54 comprises a focused energy source 58, such as a low-power laser and/or an ultrasound emitter, which can be pointed by the subject at an object 56 towards which the subject desires the limb to move. In a preferred embodiment, source 58 is coupled to the subject's eyeglasses 60. In another preferred embodiment, such as for use by a severely disabled subject, source 58 is directed responsive to motions of the subject's tongue, using techniques which are generally known in the art.

Device 54 additionally comprises one or more energy detector units 62, which are coupled to the subject's limb, elsewhere on the subject's body, and/or to fixed locations in the subject's environment (e.g., on the walls of each room in her home). Detector units 62 are preferably designed to preferentially detect the energy emitted from source 58, typically by responding to a characteristic wavelength and/or repetition rate of the energy source. Preferably, control unit 68 analyzes detector signals generated by detector units 62, so as to determine the location in space of object 56, and uses apparatus and techniques known in the art to determine a motion vector suitable for smoothly decreasing the distance between the subject's limb and object 56. The control unit subsequently drives the electrodes in array 64 to apply appropriate currents to motor nerve 66, monitors movement of the limb towards object 56, and modifies the stimulation parameters in real time so as to ensure a smooth closure on target.

Figure 5A:
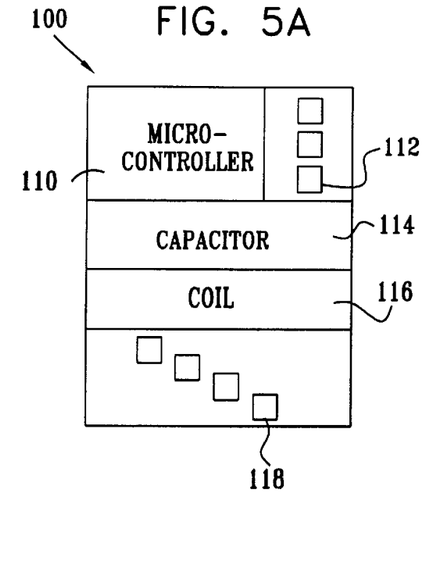
FIGS. 5A, 5B, 5C, and 5D are schematic illustrations of controllers for one or more electrode arrays, in accordance with respective preferred embodiments of the present invention.
Figure 5B:
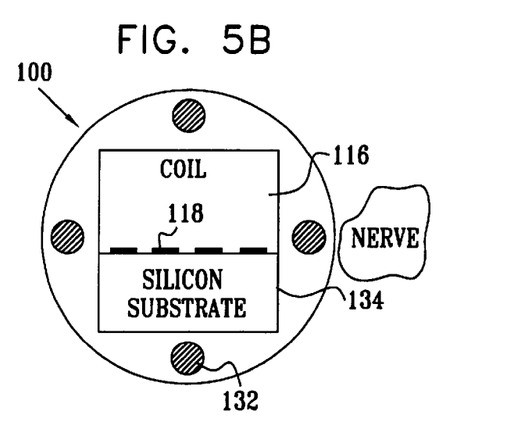
Figure 5C:
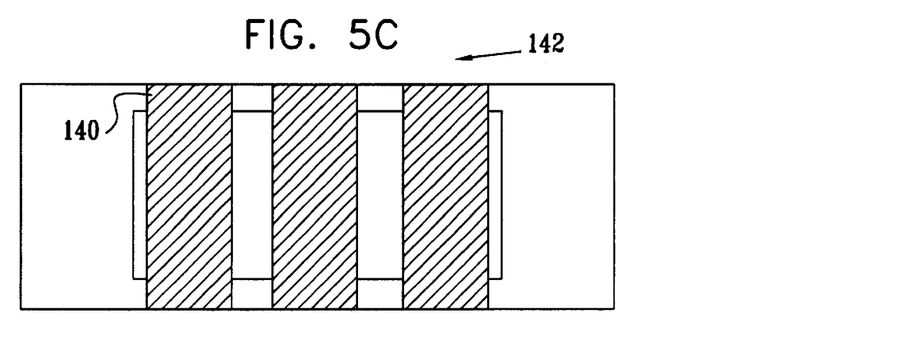
Figure 5D:
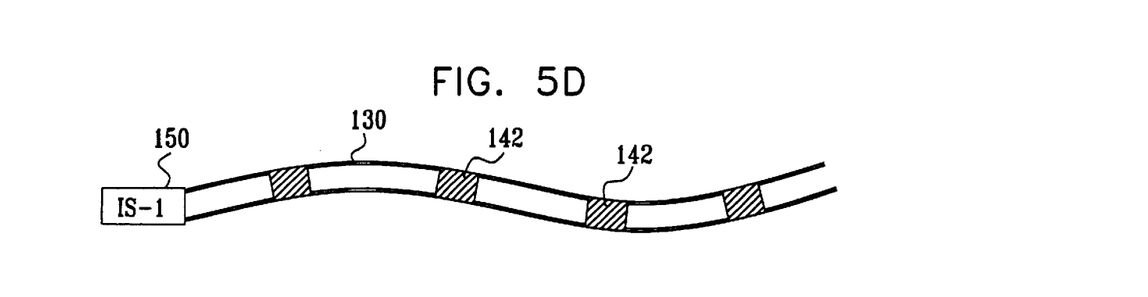

Reference is now made to FIGS. 5A, 5B, 5C, and 5D. FIG. 5A is a schematic illustration of a controller 100 for an electrode array, in accordance with a preferred embodiment of the present invention. FIG. 5B is a schematic illustration of a cross-sectional view of controller 100, in accordance with a preferred embodiment of the present invention. FIG. 5C is a schematic illustration of an outer surface of an assembly 142, comprising controller 100 and electrodes 140 coupled thereto for contacting or surrounding a nerve 130, in accordance with a preferred embodiment of the present invention. FIG. 5D is a schematic illustration showing an IS-1 connector 150 coupled to enable communication between control unit 44 (not shown) and a plurality of assemblies 142, disposed at respective positions along the length of a nerve 130, in accordance with a preferred embodiment of the present invention. It is to be understood that although the embodiments shown in FIGS. 5A, 5B, 5C and 5D are described herein with respect to particular details of construction, these represent but certain preferred modes of carrying out the present invention.

With reference to FIGS. 5A and 5B, controller 100 preferably comprises an ASIC micro-controller 110, a capacitor 114, typically having a capacitance of greater than about 10 uF, and an inductive coil 116, typically having an inductance greater than about 50 uH. Additionally, controller 100 preferably comprises four contacts 118, each typically 0.2 mm×0.2 mm, which are coupled by four respective leads 132 (e.g., MP35N wires) to control unit 44. Preferably, but not necessarily, laser welding of the leads to nickel deposits on contacts 118 provides mechanically and electrically stable coupling of the leads to the contacts. Similarly, three stimulation electrodes 140 are preferably laser welded to nickel deposits on respective contacts 112, and are driven by micro-controller 110 to apply signals to nerves as described herein. Preferably, controller 100, as shown in FIG. 5A, is approximately 3.0 mm×1.5 mm. Further preferably, size reduction of controller 100 is achieved using flip-chip methods of construction, as are known in the art.

In the cross-sectional view of controller 100 shown in FIG. 5B, it is seen that contacts 118 overlay a silicon substrate 134, typically approximately 1.5 mm×0.6 mm. Preferably, controller 100 is encased within a biologically inert silicone rubber tube 130, having an outer diameter of approximately 2.33 mm. Tube 130 additionally provides passage for four leads 132 which typically run, coiled, down the length of the tube, thereby coupling control unit 44 to each assembly 142 (FIG. 5D). It is noted that, unlike techniques known in the art, the placement of each of contacts 118 offset with respect to each other (as shown in FIG. 5A) allows for reduced mechanical stresses when coiled leads 132 are laser welded to the contacts.

Preferably, the four leads 132 are respectively dedicated to power, ground, transmit, and receive. An additional, optional, clock line, while useful for some applications, is not considered to be a necessary element to couple control unit 44 to independently control each of the micro-controllers. Instead, the four leads are controlled to act as an asynchronous serial bus, in which each micro-controller 110 coupled to the bus is adapted to drive current through its electrodes only if a particular code is received, e.g., a predetermined sequence of logical 0's and 1's on the lead designated for transmit. In this manner, only four wires are typically used to drive a plurality of controllers to apply respective desired currents to different sites on nerve 130. Thus, for example, control unit 44 can drive the micro-controllers to apply energy to the nerve in a wave, as described hereinabove, and to configure the wave in order to selectively modify the behavior of axons of a certain diameter. Advantageously, the direction of the wave can be set so as to affect substantially only afferent or efferent axons. It is noted that this ability to selectively address any electrode with only four leads makes feasible the placement of a relatively large number of independently-controlled electrodes (for example, fifteen) without requiring a correspondingly large and thus impractical number of leads.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus for treating tremor of a muscle, comprising: a plurality of electrodes, which are adapted to be placed in a vicinity of a nerve that innervates the muscle; a sensor, which is adapted to generate a signal responsive to tremor of the muscle; and
a control unit, which is adapted to receive the signal and, responsive thereto, drive the electrodes to apply a current to the nerve, configured so as to selectively stimulate afferent axons of the nerve and reduce efferent stimulation of the muscle.

2. Apparatus according to claim 1, wherein the sensor comprises one of the plurality of electrodes.

3. Apparatus according to claim 1, wherein the plurality of electrodes are adapted to be disposed at respective sites along the length of the nerve.

4. Apparatus according to claim 3, wherein the control unit is adapted to drive the electrodes in a sequence responsive to the proximity of each electrode to a brain of a subject having the tremor.

5. Apparatus according to claim 1, wherein the sensor comprises at least one electromyographic (EMG) electrode.

6. Apparatus according to claim 5, wherein the at least one EMG electrode comprises two EMG electrodes, respectively adapted to be coupled to sense electrical activity of the muscle and a muscle antagonistic thereto.

7. A method for treating tremor of a muscle, comprising: sensing tremor of the muscle; and responsive thereto, applying a current to a nerve that innervates the muscle, configured so as to selectively stimulate afferent axons of the nerve and reduce afferent stimulation of the muscle.

8. A method according to claim 7, wherein sensing the tremor comprises detecting electrical activity of the nerve.

9. A method according to claim 7, wherein sensing the tremor comprises detecting electrical activity of the muscle.

10. A method according to claim 9, wherein detecting the electrical activity of the muscle comprises detecting electrical activity of the muscle and of a muscle antagonistic thereto.

11. A method according to claim 7, wherein applying the current comprises applying the current at respective sites along the length of the nerve.

12. A method according to claim 11, wherein applying the current at the respective sites comprises applying the current in a sequence, responsive to the proximity of each site to a brain of a subject having the tremor.

* * * * *